US006666067B2

United States Patent
Stolper

(10) Patent No.: US 6,666,067 B2
(45) Date of Patent: Dec. 23, 2003

(54) VISUAL GAS SHOW IDENTIFICATION METHOD

(76) Inventor: Kathy Karol Stolper, 28875 Cragmont Dr., Evergreen, CO (US) 80439

( * ) Notice: Subject to any disclaimer, the term of this patent is extended or adjusted under 35 U.S.C. 154(b) by 0 days.

(21) Appl. No.: 09/876,685

(22) Filed: Jun. 7, 2001

(65) Prior Publication Data

US 2002/0194896 A1 Dec. 26, 2002

(51) Int. Cl.$^7$ .................. G01N 33/497; G01N 1/00; G01N 33/24
(52) U.S. Cl. .............. 73/19.01; 73/19.09; 436/175
(58) Field of Search ................ 73/19.01, 19.09; 422/68.1; 436/175, 177

(56) References Cited

U.S. PATENT DOCUMENTS 3,418,841 A * 12/1968 Issenmann .............. 73/19.01
5,152,175 A * 10/1992 Reynolds ............... 73/19.01

OTHER PUBLICATIONS

Dublyansky et al., "Epigenetic quartz–opal–calcite crusts in the Yucca Mountain subsurface; fluid inclusion and stable isotopic evidence of hydrothermal origin", Oct. 1998, Abstracts with Programs—Geological Society of America vol 30, p. 79.*
Kuboi, Toru, "Measurement of Gas Flux from the Soil Surface", Research Report from the National Institute for Environmental Studies, 1986, no month, No. 94, pp. 34–48 and English language abstract.*
K. K. Stolper: "Cuttings Analysis—An Integral Support Tool for Exploration and Exploitation" Innovative Applications of Petroleum Technology in the Rocky Mountain Area 1997; pp. 147–154 The Rocky Mountain Association of Geologists 820 16th Street, Suite 505 Denver, Colorado 80202.

* cited by examiner

Primary Examiner—Edward Lefkowitz
Assistant Examiner—Michael Cygan

(57) ABSTRACT

The abundance of methane, from a rock sample recovered from a subsurface formation, is determined by submerging the rock sample in a container with aqueous acid solution for release of natural gas from the rock sample and then determining the amount of released gas contained in submerged gas bubbles adhering to undisolved portions of the rock sample and the container as a measure of the amount of methane released from the rock sample. The relative abundance of methane from each of plurality of rock samples, treated with aqueous acid solution as described above, is determined by comparing the amount of gas contained in the adhering submerged gas bubbles from each rock sample with the amount of gas contained in adhering submerged gas bubbles from each of the other rock samples of the plurality of rock samples as a measure of the relative abundance of methane in each rock sample. Subsurface earth formations are characterized, based upon the relative abundance of methane determined for rock samples recovered from the subsurface formations.

1 Claim, 2 Drawing Sheets

VISUAL GAS SHOW IDENTIFICATION METHOD

BACKGROUND OF THE INVENTION

1. Field of the Invention

The present invention relates to methods for determining the abundance of methane in rock samples recovered from subsurface earth formations and for characterizing the subsurface formations based upon the relative abundance of methane contained in the rock samples recovered therefrom. Particularly, the present invention relates to methods for releasing and measuring the amount of methane retained in rock samples recovered from subsurface formations and characterizing the subsurface formations according to the relative abundance of methane in the rock samples recovered therefrom. Subsurface formations characterized as containing a relatively great abundance of methane by the methods of the present invention may then be considered as prospective for containing commercial deposits of natural gas.

2. Background of the Invention

Most natural gas deposits of commercial interest are comprised predominantly of methane. Such natural gas deposits also contain varying proportions of other fluids, such as carbon dioxide, hydrogen sulfide and other low molecular weight hydrocarbons. Methane is presently a major energy source in the United States of America and in other countries, and will become a more important energy source in the future. Thus, finding additional commercial deposits of methane containing natural gas is becoming increasingly important.

Over the years, a major portion of commercially producible natural gas deposits, in high permeability subsurface formations located onshore in the United States of America, have been discovered and are being produced. Exploration activity is now being directed to locating commercially producible natural gas deposits in lower permeability subsurface formations. It is expected that most future natural gas reserves found onshore in the United States of America will be found in subsurface formations having permeabilities of about 4 millidarcies, (md), or less. Formations having permeabilities as low as 0.001 md have been economically produced. With the depletion of existing natural gas reserves, new natural gas reserves in low permeability subsurface formations will have increasing economic importance.

Deposits of natural gas in low permeability subsurface formations are often huge, but are notoriously difficult to locate. Such deposits of natural gas in low permeability subsurface formations most often do not occur in anticlinal traps which can be reliably found using current exploratory techniques, such as seismology. And, such deposits must be sought using subsurface techniques such as well logging and analysis of drill cuttings and core samples. One such technique comprises analyzing rock samples recovered from subsurface formations during drilling operations for the presence of natural gas. Such rock samples commonly comprise drill cuttings and core samples. The rock samples are analyzed to determine relative abundances of natural gas therein and thereby identify subsurface formations which are prospective for containing commercial deposits of natural gas. Subsurface formations identified as containing relatively great abundance of natural gas, based upon relative abundance of natural gas in rock samples from the subsurface formations, are then subjected to additional technical and economic methodologies, such as geophysics, structural studies, stratigraphy, land acquisition and pipe line access, for selecting the subsurface formations which are prospects for containing commercial deposits of natural gas.

Natural gas is contained within pores of the rock matrix which comprise subsurface formations. The size of such pores varies considerably, from the millimeter range and larger in high permeability formations to the millimicron range or smaller in low permeability formations. The smaller the pores, the tighter natural gas is held within the rock matrix of a formation. Natural gas readily escapes from rock samples recovered from high permeability subsurface formations. However, natural gas does not readily escape from rock samples recovered from low permeability subsurface formations, and may be retained in the rock samples for extended periods of time. It is well known to analyze rock samples from low permeability subsurface formations to determine the relative abundance of hydrocarbon fluids, including natural gas, in such rock samples.

Known methods for analyzing rock samples to determine hydrocarbon fluid content include physical crushing or thermally decrepitation of rock samples under conditions of reduced pressure, or vacuum, for releasing hydrocarbon fluids as vapors. The hydrocarbon vapors are then analyzed, by means such as mass spectrometry or gas chromatography, for determining the relative abundance and composition of hydrocarbon fluids in the rock samples. The cost of equipment required for such analyses is high, as is the cost for housing and operating the equipment. Also, for low permeability rock samples, crushing the rock samples will not release substantial portions of the natural gas and other hydrocarbons from the small, (millimicron range), pores. Further, heat decrepitation of rock samples tends to produce extraneous gasses as a result of thermal degradation of inorganic minerals and thermal cracking of heavier hydrocarbons in the rock samples.

A method for rapidly and inexpensively determining the relative abundance of methane in rock samples from low permeability subsurface formations, and for the subsequent characterization of the subsurface formations based upon the relative abundance of methane in the rock samples will be particularly useful for identifying subsurface formations which are prospects for containing commercial deposits of natural gas.

SUMMARY OF THE INVENTION

Now, according to the present invention, a method is disclosed for determining the abundance of methane in rock samples recovered from subsurface formations, which method comprises:

a) selecting a rock sample recovered from a subsurface formation, for testing to determine the abundance of methane therein;

b) completely submerging the rock sample in an aqueous acid solution within a container having interior walls and bottom, for a time sufficient to dissolve at least a portion of the rock sample and releasing natural gas from the rock sample;

c) determining the amount of gas contained in bubbles retained in the container as a measure of the abundance of methane contained in the rock sample.

The method of the present invention further comprises:

d) characterizing the subsurface formation from which the rock sample was recovered based upon the relative abundance of methane in the rock sample.

The method steps a) through d) may be repeated for a plurality of rock samples from a plurality of subsurface formations and each of the subsurface formations characterized based upon the relative abundance of gas bubbles, (methane), released from the rock sample recovered from each subsurface formation.

According to the present invention, I have discovered that gas bubbles, released from a rock sample by reaction of aqueous acid solution and retained in the container, substantially comprise methane. Thus, the volume of gas in such bubbles is an indication of the abundance of methane contained in the rock sample treated according to the method of the present invention.

DETAILED DESCRIPTION OF THE INVENTION

Figure 1:
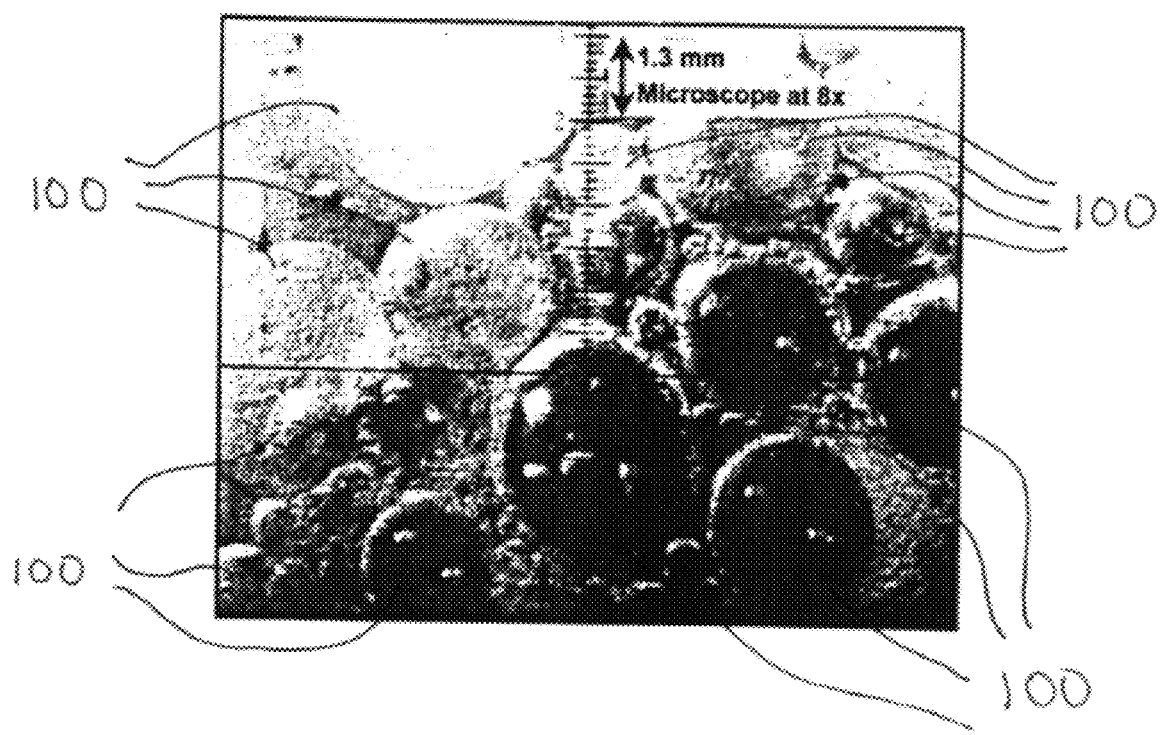
FIG. 1 is a photograph showing gas bubbles from a rock sample treated according to the method of the present invention, which rock sample was recovered from a subsurface formation which produced natural gas in commercial quantities.

The description of the invention which follows is given in terms of preferred embodiments, and it is to be understood that variations and modifications to the preferred embodiments may be made without departing from the spirit and scope of the present invention.

The present invention provides an effective reconnaissance exploratory method for characterizing low permeability subsurface formations, based upon the relative abundance of methane found in rock samples recovered from the subsurface formations, for use in identifying subsurface formations which are prospects for containing commercial deposits of natural gas.

Rock samples to which the method of the present invention may be usefully applied are those which retain substantial amounts of natural gas present when the rock samples are recovered from subsurface formations, and which disintegrate sufficiently in aqueous acid solutions to release a substantial amount of such retained natural gas. The method of the present invention may be usefully applied to both clastic and carbonate rock samples.

Rock samples contemplated herein are generally recovered from subsurface formations as core samples or drill cuttings. The great majority of such rock samples are drill cuttings recovered as a well is being drilled. Such rock samples are commonly identified according to the depth and location from which the rock samples are recovered and are identified with the subsurface formation from which the rock samples are recovered.

Drill cuttings are recovered from drilling fluid returning to the surface during the drilling of a well. The drill cuttings are generally washed in plain water to remove residual drilling fluid and dried in air or under low wattage incandescent lights. Samples of the drill cuttings are then packaged, usually in paper envelopes, marked to show the depth, location and subsurface formation from which they were recovered and the rock samples are then stored. Core samples are recovered from the walls of well bores. Core samples are generally sent to laboratories for study and then packaged and stored. Samples of drill cuttings and core samples from wells are often stored in established repositories for extended periods of time. For example, samples of drill cuttings and core samples from several million wells, drilled in the period from the 1930's or earlier to date, are stored in established repositories throughout the United States of America, such as in The Core Repository at U.S.G.S. in Denver, Colo. These rock samples, stored in repositories, comprise a huge inventory of rock samples to which the method of the present invention may be applied. Thus, the method of the present invention presents the opportunity for quickly and inexpensively identifying many deposits of natural gas which may be commercially productive.

For effective application of the method of the present invention, rock samples employed must retain a substantial amount of the natural gas present when the rock samples are recovered from the subsurface formations. Natural gas is contained within pores of subsurface formations and the rock samples recovered from such formations. Natural gas dissipates more readily from rock samples having larger pores than from rock samples having smaller pores. Consequently, for determining meaningful relative abundance of methane among a plurality of rock samples, the rock samples should have similar distribution of pore sizes and be of similar age since recovery from their subsurface formations, such that the rock samples will have retained similar amounts of natural gas present when the rock samples were recovered.

Natural gas contained in micro pores of rock samples appears to be effectively trapped and dissipates at a slower rate from rock samples having larger amounts of microporosity than from rock samples having lesser amounts of microporosity. The natural gas dissipates more slowly from rock samples having larger amounts of microporosity due to a combination of low permeability of the rock samples, wetability of the rock samples and high natural gas surface tension in the micropores. I have found that the rate at which natural gas dissipates from rock samples appears directly related to permeability of the rock samples, thus providing a convenient criteria for selecting rock samples which are useful in the method of the present invention. Permeability of rock samples can be measured by laboratory methods which are well known and widely practiced or can be estimated by applying comparative techniques, such as the Sneider Classification System For Clastics as set-out in Table 1.

TABLE 1

R. M. Sneider

CLASSIFICATION SYSTEM for CLASTICS

TYPES IA, IB, IC & ID

Very abundant to common visible porosity.
Very abundant to common pinpoint porosity.
Some pore throats visible.
Grains easily dislodged from rock surface with needle probe to reveal pores
Reservoir quality rock capable of producing gas without natural or TABLE 1-continued R. M. Sneider CLASSIFICATION SYSTEM for CLASTICS artificial stimulation, (if of adequate thickness).
IA > 100 md permeability
IB 10–100 md permeability
IC 1–10 md permeability
ID 0.5–1 md permeability
TYPE II Scattered visible porosity.
Abundant to common pinpoint porosity.
Grains occasionally dislodged from rock surface with needle probe.
Reservoir quality rock capable of producing gas if it is: of adequate thickness; interlayered with Type I; has naturally occurring fractures; and/or artificially fractured.
Permeability range is >0.07 to 0.5/1.0 md , dependent upon grain size, sorting and clay content.
TYPE III Very isolated to no visible porosity.
Little or no pinpoint porosity, few scattered pores possible.
Usually very well consolidated and/or having abundant pore-filling material such as clay.
Not usually reservoir quality being too tight to produce at commercial rates with natural or artificial fractures nor with interlayered type I rock.

The method of the present invention may be applied with particular effect to rock samples recovered from subsurface formations having permeabilities of about 4 millidarcies, (md), or less. Future reserves of natural gas are expected to be found in subsurface formations having such low permeabilities and rock samples from such low permeability formations have sufficient microporosity to retain substantial amounts of natural gas for extended periods. Rock samples from such low permeability subsurface formations may retain substantial amounts of natural gas for periods up to 35 years or more. Consequently, a large inventory of rock samples, now stored in repositories are available for testing according to the method of the present invention for locating deposits of natural gas which may be commercially producible.

According to the method of the present invention, a rock sample recovered from a subsurface formation is reacted with aqueous acid solution for releasing natural gas from the rock sample and the amount of methane released from the rock sample is determined for establishing the abundance of methane in the rock sample. In a preferred embodiment of the present invention, a rock sample is completely submerged in a container with aqueous acid solution for dissolving minerals, primarily carbonates, from the rock sample and releasing natural gas therefrom. Methane released from the rock sample forms bubbles in the aqueous acid solution which bubbles adhere to portions of the rock sample and to the walls of the container and are thus retained in the container, below the surface of aqueous acid solution. Other gases, (for example, $CO_2$, and $H_2S$), do not form such bubbles and escape the container. The bubbles retained in the container comprise substantially methane, as shown by gas chromatography.

For determining the relative abundance of methane contained in individual samples of a plurality of rock samples, the rock samples of substantially the same weight are selected for treating according to the method of the present invention. Each rock sample is treated with aqueous acid solution and the amount of gas in bubbles retained in the container is determined. Then, the relative abundance of methane in each rock sample is established by comparing of the volume of bubbles from each rock sample to the volume of bubbles from the other rock samples and ranking the rock samples from most abundant to least abundant amount of gas in the bubbles from each rock sample. As the gas in the bubbles released from each rock sample is substantially methane, this ranking is equivalent to a ranking of the rock samples according to the relative amount of methane each rock sample contains.

From this ranking of rock samples according to the relative amount of methane each rock sample contains, the subsurface formation from which each rock sample was recovered can be characterized as having more or less potential for containing commercial deposits of natural gas. Such ranking of the rock samples for relative abundance of methane and the characterization of their subsurface formations produce qualitative results. That is, conditions outside the control of a person performing the method of the present invention, such as permeability of rock samples, their treatment during recovery from the subsurface formations, and the conditions and time of their storage, all affect the amount of gas which will be present in rock samples when they are treated according to the method of the present invention. Also, subsurface formations cannot be characterized directly as commercial prospects since other factors besides the relative abundance of methane in rock samples recovered from the subsurface formations affect the commercial prospects of subsurface formations, such as formation thickness and areal extent, land availability, pipeline access. Consequently, characterizing subsurface formations based upon the relative abundance of methane in the rock samples according to the method of the present invention serves to identify subsurface formations which are worthy of further study to determine whether the subsurface formations have prospects for commercial production of natural gas. Likewise, such characterization of subsurface formations according to the method of the present invention serves to identify subsurface formations which have little prospect for commercial natural gas production.

For use in the method of the present invention, rock samples in the range of about 0.05 to about 0.1 gram are preferred. The rock samples may be in one or more pieces. For rock samples greater than about 0.10 grams, the amount of gas released may be so great that methane bubbles may dislodge and escape from the container. Rock samples of less than about 0.05 grams may not release sufficient methane for reliable determination of the amount of methane released.

Containers in which the method of the present invention may be carried out are those in which bubbles of methane released from rock samples will be retained and preferably, in which the bubbles can be visually observed for determining the abundance of methane released from the rock samples. Clear glass spot plates are preferable containers. Such spot plates are of sufficient size to contain the bubbles of gas released from rock samples in the preferred range of 0.05 to 0.10 grams and have an open top through which the bubbles may be visually observed. Such spot plates are articles of commerce and can be obtained from scientific supply houses. Prior to use, the spot plates should be cleaned by rinsing in plain water, wiping with a cotton cloth for removal of any residue and drying with a cotton or paper towel.

The aqueous acid solutions, in which the rock samples are submerged in the method of the present invention, are those which will dissolve carbonate minerals in the rock samples for release of natural gas from the rock samples under normal room conditions of temperature. A preferred aqueous acid solution is about 10% HCl in water. Aqueous acid solutions of less than about 7% HCl may not release the natural gas in a reasonable time. Aqueous acid solutions of greater than about 12% HCl may create a vigorous reaction which will dislodge methane bubbles from the container. Sufficient aqueous acid solution to completely submerge the rock samples is to be used. Insufficient acid solution may allow escape of methane from unsubmerged portions of the rock sample.

Reaction of rock samples with aqueous acid solution is preferably carried out at about normal room temperature and pressure. Higher temperatures may increase the vigor of reaction sufficiently to dislodge methane bubbles from the container. Lower temperatures may unduly retard the rate of reaction. Higher or lower pressures do not substantially affect the reaction.

Reaction of aqueous acid solution with the rock samples is preferably allowed to continue until substantially all the carbonate in the rock sample is reacted to ensure release of substantially all natural gas from the rock sample. Time for substantially complete reaction, at the preferred reaction conditions and preferred sample sizes, will be in the range of about 1 to 4 minutes. Incomplete reaction of carbonate in a rock sample may fail to release substantially all the natural gas from the rock sample.

In the method of the present invention, bubbles of gas retained in the container are substantially comprised of methane, as has been shown by chromatographic analysis. The volume of gas in the bubbles is indicative of the methane content of the rock samples and, by extension, provide a qualitative measure of the amount of methane present in subsurface formations from which the rock samples were recovered.

As described above, the relative abundance of methane in rock samples may be determined by comparing the amount of gas in bubbles released from each member of a plurality of rock samples treated according to the method of the present invention to the amount of gas in bubbles released from the other rock samples of the plurality of rock samples, then ranking the rock samples as containing from most abundant to least abundant amounts of gas in the bubbles. Gas in the bubbles has been determined to substantially comprise methane.

The amount of each rock sample to be tested according to the method of the present invention may conveniently be determined by weighing on a laboratory balance. The amount of gas in the bubbles of gas released from the rock samples may be determined by either quantitative or qualitative measure. Preferably, the amount of gas in bubbles of gas released from rock samples is determined by visual observation. The bubbles may be visually observed either with or without magnification. However, the bubbles are preferably observed under magnification, such as through an 8× binocular microscope. Microscopes having calibration lines are particularly useful for determining the size of gas bubbles which vary in size from submillimeter to several millimeters in diameter. As a qualitative measure, the amount of gas in bubbles from a rock sample is adequate for determining the relative abundance of methane in the rock sample A determination of the actual volume of gas in the bubbles is not necessary, although the actual volume may be determined if desired. A qualitative measure of the amount of gas in the bubbles can be made by determining the number and size of gas bubbles from a rock sample. That is, the relative abundance of methane released from rock samples can be determined by visually comparing the number and size of gas bubbles released from one rock sample to the number and size of gas bubbles released from one or more other rock samples, thereby determining whether the amount of gas in the bubbles from one rock sample is more abundant or less abundant than the amount of gas in the bubbles from the other rock samples. In such determinations, bubbles of less than about 0.2 mm may be ignored as such small bubbles contain only a very small amount of gas. Such small amounts of gas will not affect the ultimate purpose of the determination of the relative abundance of gas in the rock samples, which is to characterize subsurface formations which are of interest for containing commercial quantities of natural gas.

Preferred methods of the present invention, for determining the relative amounts of methane released from rock samples and therefrom characterizing subsurface formations based upon the relative abundance of methane released from rock samples recovered from the subsurface formations, are set out in the Examples below.

EXAMPLE 1

In this example, two rock samples from the Niobrara carbonate formation in Yuma County, Colo. were treated with aqueous acid solution and the bubbles of gas released form the rock samples were visually observed to determine the relative abundance of methane released from each rock sample.

Rock sample "A" was recovered from the Niobrara carbonate formation at a depth of 1506' from the well 1-Strangeways, 14-2S-43W, Beecher Island Field, Yuma County, Colo. in the year 1936. The rock sample had been stored since that date as described above. The cumulative production from the field was 42 BCF natural gas as of December, 1998.

Rock sample "B" was recovered from the Niobrara carbonate formation at 1910' from well Whomble 1-Whomble, 35-2S-44W, Yuma County, Colo. in the year 1956. The rock sample had been stored since that date as described above. The well was abandoned as non productive.

In this Example, about 0.075 grams of each rock sample was placed in a depression of a clear glass spot plate. Each rock sample was completely submerged in 10% HCl aqueous acid solution at room temperature and pressure. Reaction of the acid solution with each rock sample was allowed to continue for about 2 minutes, by which time the reaction of acid solution with each rock sample appeared, by visual observation, to be essentially complete.

Bubbles released from each rock sample accumulated in the depressions in the spot plate and were then photographed under 8×magnification. Gas from bubbles from rock sample 'A' were analyzed by gas chromatography and found to substantially comprise methane.

FIG. 1 of the drawings is a reproduction of the photograph of gas bubbles from rock sample "A". In FIG. 1, the gas bubbles 100 are large in number and size, as is clearly seen.

Figure 2:
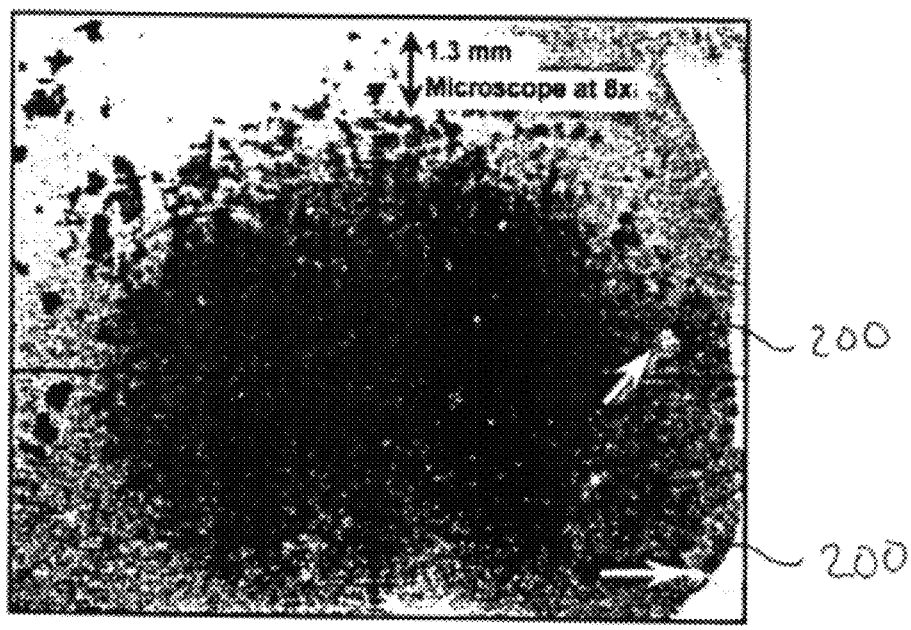
FIG. 2 is a photograph showing gas bubbles from a rock sample treated according to the method of the present invention, which rock sample was recovered from a subsurface formation which does not contain natural gas in commercial quantities.

FIG. 2 of the drawings is a reproduction of the photograph of gas bubbles from rock sample "B". In FIG. 2, the gas bubbles 200 are small in number and small in size.

Visual comparison of the number and size of gas bubbles 100 from rock sample "A" to the number and size of gas bubbles 200 from rock sample "B" clearly shows that rock sample "A" contained a relatively great abundance of methane compared to the abundance of methane from rock sample "B".

It is to be noted that rock sample "A" had been recovered about 60 years before the gas show test of Example 1 was performed, and rock sample "B" had been recovered more than 30 years before. The rock samples had been stored in a repository since their recovery, as described above. This demonstrates that rock samples can retain substantial amounts of natural gas for substantial periods of time and that the methods of the present invention can be applied to such rock samples for identifying subsurface formations which may be prospects for containing commercial deposits of natural gas.

EXAMPLE 2

This Example shows a preferred embodiment of the present invention for characterizing subsurface formations, based upon relative abundance of methane in rock samples from such formations, to identify subsurface formations worthy of further study to find those which are prospects for containing commercial deposits of natural gas.

In this Example, several hundred rock samples from subsurface formations of known productive history were treated according to the method of the present invention employed in Example 1 and photographs of the gas bubbles from each rock sample were made.

The subsurface formations were typed, according to their productive history, into the following groups:

Type "A" Abundant: commercial gas production

Type "B" Moderate: gas production with moderate water production

Type "C" Scattered: minor gas production, predominant water production

Type "D" Zero to Trace: water production

Figure 3:
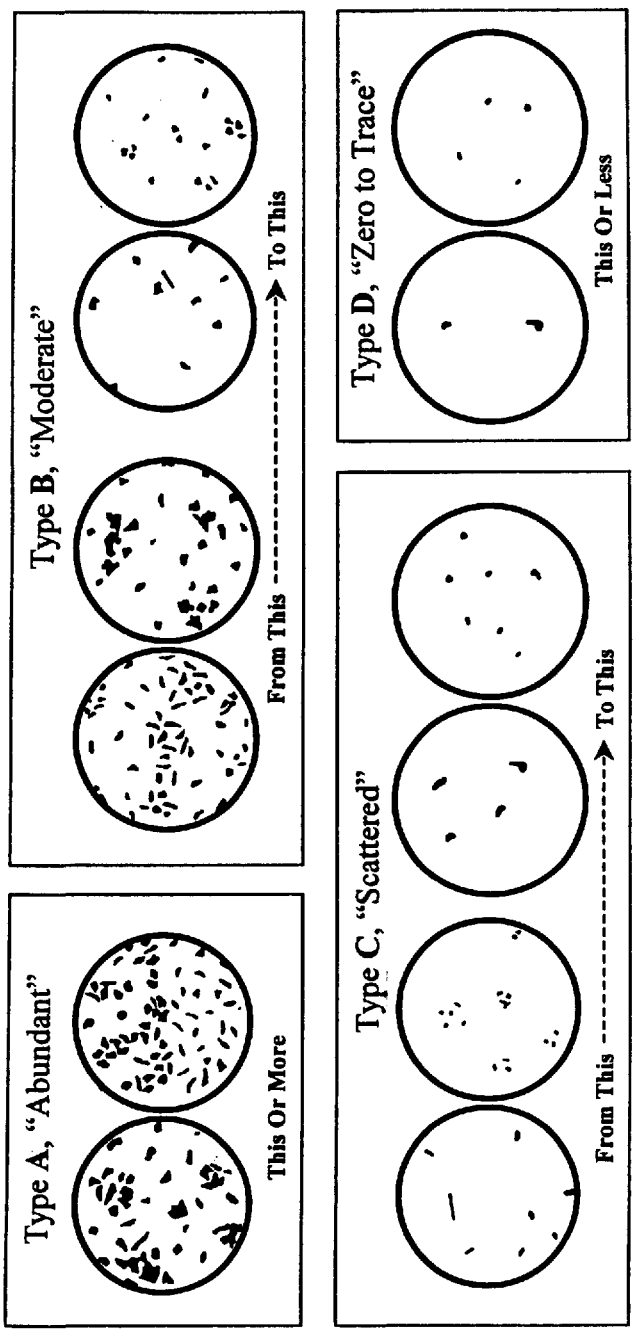
FIG. 3 illustrates a Standard Estimation Chart developed from information obtained by treating rock samples according to the method of the present invention, which Standard Estimation Chart is useful for characterizing a subsurface formation based upon the relative abundance of methane released from a rock sample recovered from the subsurface formation.

Photographs of the gas bubbles from the rock samples were then arranged in groups according to the Types of the subsurface formations from which the rock samples were recovered. From the photographs, a visual Standard Estimation chart was prepared, showing the range of abundance and size of bubbles for rock samples corresponding to each type of subsurface formation set out above. FIG. 3 of the drawings shows the Standard Estimation Chart so prepared.

Additional rock samples from additional subsurface formations of known productive history were then obtained. The rock samples were treated with aqueous acid solution according to the method of Example 1. Photographs of the bubbles from each rock sample were visually compared to the Standard Estimation Chart and each subsurface formation was assigned a Type designation based upon the abundance of gas bubbles from the rock samples as compared to the Standard Estimation Chart. The Type designations of the subsurface formations, as determined from the Standard Estimation Chart, were then compared to the actual natural gas production histories of the subsurface formations.

TABLE 2

Comparison of Subsurface Formations Type designations from the Standard Estimation Chart with Subsurface Formations' Known Production History

| Subsurface Formations | Type designation From Standard Estimation Chart | Production History |
| --- | --- | --- |
| East Texas, | Type "A" Abundant | commercially productive |
| Cotton Valley tight gas sands | Type "D" Trace to Zero | non-economical (dry) wells |
| Whitney Canyon, | Type "A" Abundant | commerically productive |
| Wyoming Overthrust | Type "B" Moderate | comercially |

TABLE 2-continued

Comparison of Subsurface Formations Type designations from the Standard Estimation Chart with Subsurface Formations' Known Production History

| Subsurface Formations | Type designation From Standard Estimation Chart | Production History |
| --- | --- | --- |
| | | productive |
| Belt | Type "C" Scattered | non-commercial |
| | Type "D" Trace to Zero | non-commercial |
| Colorado, Niobrara Shaley Chalk | Type "A" Abundant | productive |
| | Type "B" Moderate | productive |
| | Type "D" Trace to Zero | water |
| Southern Oklahoma, | Type "A" Abundant | commercially productive |
| Britt Formation | Type "C" Scattered | non-productive |
| | Type "D" Trace to Zero | non-productive |
| Australia Carnavon Basin, low permeability sands | Type "A" Abundant | tested and producing |
| | Type "D" Trace to Zero | water |

Subsurface formations characterized as Type "A" Abundant or Type "B" Moderate, by comparing the gas bubbles from rock samples recovered from the subsurface formations with the Type classifications of the Standard Estimation Chart, are productive of natural gas. On the other hand, subsurface formations characterized as Type "C" Scattered or Type "D" Trace to Zero are non-productive of natural gas. Thus, Example 2 demonstrates the utility of the present invention for identifying subsurface formations which are candidates for development into prospects for commercial natural gas production.

It is to be appreciated that variations and modifications may be made to the preferred embodiments of the invention disclosed herein without departing from the spirit and scope of the invention, and no limitation to the invention is intended other than limitations included in the claims appended hereto.

I claim:

1. A method for characterizing a subsurface formation, which method comprises:

a). preparing a standard estimation chart for use in characterizing a subsurface formation to be characterized, as follows;

i) establishing a plurality of group designations based upon the known ranges of gas productivity of subsurface formations, including;

| Group | Productivity |
| --- | --- |
| "A" Group | commercial gas production |
| "B" Group | gas production with moderate water production |
| "C" Group | minor gas production with predominant water production |
| "D" Group | water production | ii) selecting a plurality of subsurface formations, each subsurface formation of the plurality of subsurface formations having a known gas production history;

iii) assigning each subsurface formation of the plurality of subsurface formations to the group of the plurality of groups which has a production designation most similar to the known gas production history of each said subsurface formation;

iv) selecting a plurality of rock samples, each rock sample of the plurality of rock samples recovered from a subsurface formation of the plurality of subsurface formations, with each rock sample of substantially the same size as the other rock samples of the plurality of rock samples;

v). assigning each rock sample of the plurality of rock samples to the group of the plurality of groups to which is assigned the subsurface formation of the plurality of subsurface formations from which each rock sample was recovered.

vi). completely submerging each rock sample of the plurality of rock samples, in a container having an interior surface, with an aqueous acid solution for releasing substantially all natural gas, comprising methane and other gasses, from each rock sample; forming accumulated, submerged gas bubbles, substantially comprising methane, adhered to the container inner surface; and allowing other gasses to escape the container;

vii). for each group of the plurality of groups, determining and preparing a visual record of the range of accumulated, submerged gas bubbles produced from rock samples of the plurality of rock samples assigned to each group;

viii). creating a standard estimation chart showing the visual records of the range of accumulated, submerged gas bubbles determined for each group of the plurality of groups;

b). selecting a rock sample recovered from a subsurface formation to be classified;

c). completely submerging the selected rock sample in a container having an interior surface with aqueous acid solution for releasing substantially all natural gas, comprising methane and other gases, from the selected rock sample; forming accumulated, submerged gas bubbles substantially comprising methane adhered to the container interior surface; and allowing other gasses to escape the container;

d). comparing the accumulated, submerged gas bubbles from the selected rock sample with the plurality of visual records of the standard estimation chart; and e). classifying the subsurface formation to be classified as being of the same group of the plurality of groups having a visual record of the range of accumulated, submerged gas bubbles most comparable to the accumulated, submerged gas bubbles produced from the selected rock sample.

* * * * *